US009593303B2

(12) United States Patent
Battles et al.

(10) Patent No.: US 9,593,303 B2
(45) **Date of Patent: *Mar. 14, 2017**

(54) **METHOD FOR CONTINUOUSLY CULTURING *EHRLICHIA* AND *NEORICKETTSIA RISTICII***

(71) Applicant: Intervet Inc., Madison, NJ (US)

(72) Inventors: Jane Kwun-Lai Battles, Dagsboro, DE (US); Kimberly D. Proudfoot, Millsboro, DE (US); Brenda L. Meding, Milton, DE (US); Patrick G. Funk, DeSoto, KS (US); R. Monty Warthen, Millsboro, DE (US); F. Randall Bethke, Millsboro, DE (US); Eric A. Ellis, Whaleyville, MD (US); Amy Y. Purse, Seaford, DE (US)

(73) Assignee: Intervet Inc., Madison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/706,283

(22) Filed: May 7, 2015

(65) Prior Publication Data

US 2015/0252320 A1 Sep. 10, 2015

Related U.S. Application Data

(62) Division of application No. 12/674,114, filed as application No. PCT/US2008/076025 on Sep. 11, 2008, now Pat. No. 9,051,557.

(60) Provisional application No. 61/031,428, filed on Feb. 26, 2008, provisional application No. 60/971,726, filed on Sep. 12, 2007, provisional application No. 60/971,716, filed on Sep. 12, 2007.

(51) Int. Cl.
*C12N 1/20* (2006.01)
*C12N 1/36* (2006.01)
*C12N 11/16* (2006.01)

(52) U.S. Cl.
CPC ................ *C12N 1/20* (2013.01); *C12N 1/36* (2013.01); *C12N 11/16* (2013.01)

(58) Field of Classification Search
None
See application file for complete search history.

(56) References Cited

U.S. PATENT DOCUMENTS

| | | | | |
|---|---|---|---|---|
| 3,616,202 | A | 10/1971 | Marble | |
| 5,192,679 | A | 3/1993 | Dawson et al. | |
| 5,401,656 | A | 3/1995 | Dawson | |
| 5,869,335 | A | 2/1999 | Munderloh et al. | |
| 5,877,159 | A | 3/1999 | Powell et al. | |
| 5,955,359 | A | 9/1999 | Dumler et al. | |
| 5,976,860 | A * | 11/1999 | Coughlin | C12N 1/20 435/243 |
| 5,989,848 | A | 11/1999 | Dawson | |
| 6,284,238 | B1 | 9/2001 | Coughlin et al. | |
| 7,767,451 | B2 | 8/2010 | Mochizuki | |
| 2003/0003508 | A1 | 1/2003 | Raoult et al. | |
| 2005/0202046 | A1 | 9/2005 | Hu et al. | |
| 2006/0057699 | A1 | 3/2006 | Munderloh | |

OTHER PUBLICATIONS

Chen et al., Infection and Immunity, Feb. 1995, vol. 63, No. 2, p. 647-655.*
Zweygarth et al., Ann. N.Y. Acad. Sci. 990:573-580 (2003).*
Dumler et al., International Journal of Systematic and Evolutionary Microbiology (2001), 51,2145-2165.*
Brouqui et al., "Cytopathic Effect, Plaque Formation, and Lysis of Ehrlichia chaffeensis Grown on Continuous Cell Lines", Infection and Immunity, Feb. 1994, 62(2): 405-411.
Fenollar et al., "Culture and Phenotypic Characterization of a Wolbachia pipientis Isolate", Journal of Clinical Micobiology, Dec. 2002, 41(12): 5434-5441.
Jarrett et al., "Determinants of the Host Range of Feline Leukaemia Viruses", Journal of General Virology, 1973, 20: 169-175.
Rikihisa, "The Tribe Ehrlichieae and Ehrlichial Diseases", Clinical Microbiology Reviews, Jul. 1991, 4(3): 286-308.
International Search Report for corresponding PCT/US2008/076025, mailed Jan. 19, 2009.
Aguirre et al., "First isolation and molecular characterization of Ehrlichia canis in Spain"; Veterinary Parasitology 125:365-372 (2004).
Keysary et al., "Cultivation of Ehrlichia Canis in a Continuous BALB/C Mouse Macrophage Cell Culture Line", Journal of Veterinary Diagnostic Investigation,13:521-523 (2001).
Breitschwerdt et al., "Doxycycline Hyclate Treatment of Experimental Canine Ehrlichiosis Followed by Challenge Inoculation with Two Ehrlichia canis Strains", Antimicrobial Agents and Chemotherapy, 42(2):362-368 (Feb. 1998).
Heimer et al., "Propagation of Granulocytic Ehrlichia spp. from Human and Equine Sources in HL-60 Cells Induced to Differentiate into Functional Granulocytes", Journal of Clinical Microbiology, 35(4):923-927 (Apr. 1997).
Heimer et al., "A Single Tissue Culture System for the Propagation of the Agents of the Human Ehrlichioses", Am. J. Trop. Med. Hyg., 58(6):812-815 (1998).

* cited by examiner

*Primary Examiner* — Irene Marx

(57) ABSTRACT

The present invention relates to a method of culturing bacterial organisms belonging to the family Anaplasmataceae in mammalian embryonic or fetal cells. In particular, the present invention is directed to growth of bacterial organisms belonging to the family Anaplasmataceae including organisms belonging to the *Anaplasma, Ehrlichia* and *Neorickettsia* genera. The bacterial organisms may be cultured in mammalian embryonic or fetal host cells including feline embryonic host cells. Bacterial material cultured according to the methods described herein may be used as the basis for vaccines against diseases associated with the Anaplasmataceae bacteria, or as the basis for diagnostic applications useful for diagnosing diseases associated with the Anaplasmataceae bacteria.

6 Claims, No Drawings

METHOD FOR CONTINUOUSLY CULTURING *EHRLICHIA* AND *NEORICKETTSIA RISTICII*

CROSS-REFERENCE TO RELATED APPLICATIONS

This application is a Divisional application of U.S. application Ser. No. 12/674,114, filed on Feb. 18, 2010, which is a national stage entry under 35 U.S.C. §371 of PCT/US2008/076025, filed on Sep. 11, 2008, which claims priority to U.S. Provisional Application Nos. 60/971,716, filed on Sep. 12, 2007, 60/971,726, filed on Sep. 12, 2007, and 61/031,428, filed on Feb. 26, 2008, the contents of which are hereby incorporated by reference in their entireties.

FIELD OF THE INVENTION

The present invention relates to a method of culturing bacterial organisms belonging to the family Anaplasmataceae in mammalian embryonic or fetal cells, such as feline embryonic or fetal cells. In particular, the present invention is directed to growth of bacterial organisms belonging to the family Anaplasmataceae including organisms belonging to the genera *Anaplasma, Ehrlichia, Neorickettsia*, and *Wolbachieae*. The bacterial organisms may be cultured in mammalian embryonic or fetal cells, such as feline embryonic or fetal host cells. Bacterial material cultured according to the methods described herein may be used as the basis for vaccines against diseases associated with the Anaplasmataceae bacteria.

BACKGROUND OF THE INVENTION

The bacteria of the family Anaplasmataceae are obligate intracellular parasites. As such, these microorganisms are often difficult to grow and the diseases they cause are difficult to diagnose. Because of the difficulty of growing these microorganisms, large-scale preparation of vaccine antigens is costly and sometimes impossible. The bacteria of the Anaplasmataceae family are pathogenic agents of vector-transmitted diseases of human and animals. They are mostly transmitted by invertebrate vectors such as ticks. Within the family Anaplasmataceae, the microorganisms of the genera *Anaplasma, Ehrlichia, Neorickettsia* and *Wolbachieae* are causative agents of vector-transmitted diseases and are difficult to grow, especially on a large-scale. Bacterial species belonging to the genus *Rickettsieae* are not included within the family Anaplasmataceae.

Anaplasmosis is a major tick-borne disease of cattle endemic in the United States. The causative agent, *Anaplasma marginale*, invades and multiplies in erythrocytes of cattle, causing mild to severe anemia. Annual mortality and morbidity due to anaplasmosis impacting beef cattle herds has caused millions of dollars worth of damage due to, for example; weight loss during acute infections and increased veterinary costs. See e.g., Palmer in Veterinary Protozoan and Hemoparasite Vaccines, J. G. Wright (Ed.) CRC Press Inc., Boca Raton, Fla. 1989.

*Anaplasma phagocytophilum* causes tick borne fever in sheep, cattle, and bison, and is vecotred by *I. ricins*. See U.S. Pat. No. 6,284,238, which is fully incorporated by reference herein. In contrast to *A. marginale* which infects red blood cells, *A. phagocytophilum* infects granulocytes.

*Ehrlichia* bacteria are closely related to *Anaplasma* species. Those species for which a biological vector is known are transmitted by ticks, such as for *E. canis*. While *Anaplasma phagocytophilum* prefers to infect granulocytes in its mammalian host, *Ehrlichia canis* prefers to infect mononuclear white blood cells. Typically, *Anaplasma* and *Ehrlichia* are contained within membrane-bound vacuoles of their respective host cells.

The first *Ehrlichia* species recognized was *E. canis*. It occurs in all areas of the world where the vector tick, *Rhipicephalus sanguineus* (the brown dog tick), lives. The disease it causes is sometimes called canine tropical pancytopenia. It is a problem especially in all warm areas of the world, e.g., the southern U.S., Central and South America, the Mediterranean, and South Asia. *Ehrlichia canis* may be cultivated in the dog cell line DH82 as well as human-dog hybrid cell lines (See Rikihisa, Y. 1991. Clinical Microbiology Reviews, 4:286). Various strains of *E. canis* are listed in U.S. Patent Application No. 2006/0188524, which is herein incorporated by reference in its entirety. *Ehrlichia chaffeensis* is associated with human ehrlichiosis. See Maeda, K. et al., 1987, N. Eng. J. Med. 316:853; Dawson, J. E. et al., 1991, J. Clin. Microbiol. 29:2741. *E. chaffeensis* can also be cultured in DH82 cells.

*Neorickettsia* bacteria are closely related to *Ehrlichia* and *Anaplasma* bacteria. *Neorickettsia* species include *N. risticii* and *N. sennetsu* (both of which were previously classified in the genus *Ehrlichia*. *N. risticii* is the causative agent of Potomac horse fever. This disease is known to occur in North America, France and India. *N. risticii* may be grown in macrophage-monocyte cell lines such as P388$D_1$, T-84 and U937. *N. sennetsu* is the causative agent of Sennetsu erlichiosis of humans. *N. sennetsu* grows in murine and human cell lines such P388D, L929, and HeLa.

Infections with bacterial organisms of the Anaplasmataceae family may be diagnosed by direct microscopic examination and/or serodiagnosis. Treatment with antibiotics may be effective. Equine vaccines to protect against *N. risticii* are commercially available. See Compendium of Veterinary Products, 6th ed., Aurora Arrioja, ed., North American Compendiums, Ltd., Port Huron, Mich. (2001). At least one cattle vaccine to protect against anaplasmosis is also commercially available. See Id. However, vaccines have not been manufactured and sold for large scale prevention of other diseases caused by bacterial organisms such as, for example, *E. canis*. Presently, it is believed that there are no commercial vaccines for *Ehrlichia canis*.

Efforts have been made to grow certain *Rickettsiale* organisms in a variety of host cells. U.S. Pat. No. 5,192,679, which is herein incorporated by reference in its entirety, relates to continuous propagation of *E. canis* in a canine monocyte macrophage cell line DH82 in an in vitro medium that supports the growth of DH82 cells. U.S. Published Application No. 2005/0202046, which is herein incorporated by reference in its entirety, relates to *E. canis* vaccines where the *E. canis* was cultured in DH82 cells. U.S. Pat. No. 5,401,656, which is herein incorporated by reference in its entirety, relates to propagation of *E. chaffeensis* and *E. canis* in an immortalized human endothelial cell line. U.S. Pat. No. 5,869,335, which is herein incorporated by reference in its entirety, relates to culturing certain *Rickettsiale* bacteria in *Ixodes scapularis* cell lines. U.S. Pat. No. 5,989,848, which is herein incorporated by reference in its entirety, relates to growth of certain Ehrlichial species on an immortalized human endothelial cell line. U.S. Pat. No. 3,616,202, which is herein incorporated by reference in its entirety, relates to growth of *Anaplasma* marginale in a rabbit bone marrow tissue culture. U.S. Published Patent Application No. 2006/0057699, which is herein incorporated by reference in its entirety, relates to growth of certain *Anaplasma* species in mammalian cells. U.S. Published Patent Application No. 2003/0003508, which is herein incorporated by reference in its entirety, relates to culturing *Rickettsia pulicis* bacterium on a *Xenopus laevis* cell line. U.S. Pat. Nos. 5,955,359 and 5,976,860, which are herein incorporated by reference in their entirety, relate to culturing certain bacterial species belonging to the Rickettsiales order in certain mammalian cell lines. U.S. Pat. No. 5,877,159, which is herein incorporated by reference in its entirety, relates to methods for introducing and expressing genes in animal cells using certain live invasive bacterial vectors.

A thesis discussing immunization of dogs against canine ehrlichiosis using inactivated *Ehrlichia canis* organisms has been submitted. Sunita Mahan, *Immunisation of German shepherd dogs against canine ehrlichiosis using inactivated Ehrlichia canis organisms*, thesis submitted to the Faculty of Veterinary Science at the University of Zimbabwe (May 1997). This thesis discusses use of a β-propiolactone inactivated *E. canis* organisms in combination with Quill A.

Because growth of bacterial species belonging to the Anaplasmataceae family in host cells has met with only limited success and apparently has not translated into an abundant supply of vaccines, there remains a general need to develop culturing systems for growing such bacterial species to facilitate the study of these pathogenic microorganisms and for the development of vaccines to guard against the diseases they cause. There is also a need to develop a large scale culturing system for preparation of large amounts of antigen from such microorganisms for use in diagnostics and vaccines.

SUMMARY OF THE INVENTION

The present invention broadly relates to culturing bacterial organisms belonging to the Anaplasmataceae family in mammalian embryonic or fetal host cells. The cultured bacterial organisms can be used as a vaccine against diseases caused by the bacterial organisms. The antigen used in the vaccine can be made from the bacterial organisms isolated from the mammalian host cells. Alternatively, the antigen used in the vaccine can be made from cultures of the mammalian host cells infected with the bacterial organisms. The bacterial organisms (or the host cell if present) can be inactivated. Alternatively, the bacterial organisms can be attenuated live such that they replicate within an animal to which they are administered one or more times without causing the disease state typical of the non-attenuated pathogenic form of the bacterial organism.

With greater particularity, the present invention relates to culturing bacterial organisms of the Anaplasmataceae family in host cells that are embryonic mammalian cells. In one embodiment of the invention, the bacteria are cultured in non-human embryonic mammalian cells. Such host cells can be obtained from any part of a non-human animal embryo or fetus. Such host cells can be differentiated or non-differentiated. The embryonic host cells can be derived from feline, canine, murine, swine, bovine, ovine, simian or equine embryos or fetuses. In one embodiment of the invention, the embryonic host cells are derived from feline embryos or fetuses.

In one embodiment of the invention, the bacterial organisms of the Anaplasmataceae family belong to the genera *Anaplasma, Ehrlichia* or *Neorickettsia*. Bacterial organisms belonging to the family Anaplasmataceae do not include those bacterial organisms belonging to the family Rickettsiaceae. (The Rickettsiaceae family includes the genus *Rickettsieae*, which includes the species *R. orientia* and *R. rickettsia*.) The specific bacterial organisms belonging to the *Anaplasma* genus can be *A. bovis, A. centrale, A. marginale*, and *A. phagocytophilum*. The specific bacterial organism belonging to the *Ehrlichia* genus can be *E. canis*. The specific bacterial organism belonging to the *Neorickettsia* genus can be *N. risticii*.

The present invention relates to a method of culturing a bacterial species from the Anaplasmataceae family comprising: i) obtaining bacterial species from the Anaplasmataceae family; ii) infecting non-human mammalian embryonic cells with said bacterial species; and iii) culturing said non-human mammalian embryonic cells under conditions conducive to propagating the non-human mammalian embryonic cells, thereby culturing the bacterial species. The bacterial species can be obtained in a purified state free of any host cell, in a state where it is present in a host cell, or in a state where it is present in a homogenate of infected animal tissue. In one embodiment, the non-human mammalian embryonic cells are infected with a homogenate of mammalian cells isolated from an animal infected with an Anaplasmataceae organism. In another embodiment, the non-human mammalian embryonic cells are infected by exposing the embryonic cells to an Anaplasmataceae organism. The Anaplasmataceae bacterial species can be from the genera *Anaplasma, Ehrlichia* or *Neorickettsia*. The Anaplasmataceae bacterial species can be *Anaplasma bovis, Ehrlichia canis*, or *Neorickettsia risticii*. In one embodiment, the non-human mammalian embryonic cells are feline cells. The feline cells can be feline embryonic fibroblast cells, FEA feline embryonic cells, or *felis catus* whole fetus cells. The non-human mammalian embryonic cells can be undifferentiated and/or immortalized. In another embodiment, the non-human mammalian embryonic cells are monkey embryo kidney epithelial cells.

The present invention also relates to compositions comprising non-human mammalian embryonic cells infected with a bacterial species from the Anaplasmataceae family. The bacterial species can be from the genera *Anaplasma, Ehrlichia* or *Neorickettsia*. The Anaplasmataceae bacterial species can be any known to the skilled artisan including, without limitation, *Anaplasma bovis, Anaplasma phagocytophilum, Ehrlichia canis*, or *Neorickettsia risticii*. The non-human embryonic mammalian cells can be feline embryonic fibroblast (FEF) cells, FEA feline embryonic cells, or *felis catus* whole fetus cells. The non-human mammalian embryonic cells can be undifferentiated and/or immortalized. The non-human embryonic mammalian cells can also be monkey embryo kidney epithelial cells.

The present invention also relates to methods of preventing infection in a mammal by administering to the mammal a vaccine based upon material cultured according to the methods described herein. The present invention also pertains to methods of protecting a mammal by administering to the mammal a vaccine based upon material cultured according to the methods described herein. The present invention also pertains to methods of treating a mammal by administering to the mammal a vaccine based upon material cultured according to the methods described herein. In particular, the present invention relates to protecting a mammal against a disease caused by an organism belonging to the family Anaplasmataceae by providing to the mammal a therapeutically effective amount of a Anaplasmataceae bacterial antigen. The mammal can be a human, monkey, cat, dog, horse, cow, pig, sheep or goat. In one embodiment of the invention, the animal is a dog.

The present invention also pertains to administering to a mammal an immunologically protective amount of material cultured according to the methods described herein; or administering to a mammal an effective amount of material cultured according to the methods described herein to produce an immune response.

DETAILED DESCRIPTION OF THE INVENTION

Unless otherwise stated, all terms used herein have their ordinary meaning as would be understood by the skilled artisan. Terms for which explicit definitions are provided below have in addition to their explicit meaning the meaning typically ascribed by the ordinarily skilled artisan.

The present invention relates to methods of culturing microorganisms. More particularly, the present invention is related to methods of growing bacterial organisms belonging to the family Anaplasmataceae. More particularly, the present invention is related to methods of continuously growing organisms belonging to the genera *Anaplasma, Ehrlichia* or *Neorickettsia.*

Non-limiting examples of species belonging to the *Anaplasma* genus that may be used according to the present invention include *A. bovis, A. centrale, A. marginale, A. ovis, A. platys* and *A. phagocytophilum* (previously referred to as *Ehrlichia phagocytophila, Ehrlichia equi*, human granulocytic ehrlichiosis agent or HGE agent). Non-limiting examples of species belonging to the *Ehrlichia* genus that may be used according to the present invention include *E. canis, E. chaffeensis*, and *E. muris*. Non-limiting examples of species belonging to the *Neorickettsia* genus that may be used according to the present invention include *N. helminthoeca, N. risticii* (Potomac horse fever, formerly termed *E. risticii*), and *N. sennetsu.*

According to the present invention, bacterial organisms of the Anaplasmataceae family are grown in mammalian embryonic or fetal host cells. As used herein, "host cells" are cells that bacterial organisms of the Anaplasmataceae family can infect and in which the bacterial organisms can replicate. Non-limiting examples of mammalian embryonic or fetal host cells include human, feline, canine, murine, swine, bovine, ovine, simian or equine embryonic or fetal cells. As used herein, "infected host cells" refer to host cells that contain one or more Anaplasmataceae bacteria.

The host cells can be derived from a single cell isolated from mammalian embryonic or fetal tissue. For example, the cells can be derived from embryonic feline, canine, bovine, equine, murine, swine, simian or human tissue.

In one embodiment of the present invention, bacterial species belonging to the Anaplasmataceae are cultured in host cells that are derived from non-human mammalian embryonic or fetal tissue. A non-limiting examples of feline embryonic or fetal cells that may be used according to the present invention include feline embryonic fibroblasts (FEF) cells, FEA feline embryonic cells (University of Glasgow, Glagow, Scotland; as described in Jarrett, O. et al., *J. gen. Prot* 20:169-175 (1973)), and *felis catus* whole fetus cells (FCWF-4, American Type Culture Collection, P.O. Box 1549 Manassas, Va. 20108, United States (hereafter, "ATCC") deposit CRL-2787).

The bacterial organisms cultured according to the present invention may be used for vaccines, diagnostics or further research including, for example, production of quantities of biological molecules for isolation and study. Accordingly, the bacteria cultured according to present invention may be formulated in a vaccine for administration to a mammal to prevent infection or ameliorate disease caused by the bacterial organism. For example, the bacteria cultured in the host cells could be *Ehrlichia canis* for use in a vaccine to be given to canines to prevent or ameliorate canine ehrlichiosis.

Hence, the present invention also relates to immunogenic compositions or vaccines based upon material cultured according to the present invention. The therapeutic agent (also referred to as the antigen, active agent, or the immunogenic composition) that can serve as the basis for a vaccine can be one or more of the following:

a) harvested cultures of host cells that are infected with Anaplasmataceae bacteria;

b) extracts or fractions of (a) that are enhanced with respect to the concentration of the Anaplasmataceae bacteria contained within the infected host cells;

c) Anaplasmataceae bacteria enhanced extracts of (a) that contain remnants of the host cells;

d) Anaplasmataceae bacteria extracts of (a) that do not contain remnants of the host cells; or e) isolated Anaplasmataceae bacterial immunogens.

"Isolated" when used herein means removed from its naturally occurring environment. Hence, isolated Anaplasmataceae bacterial cells broadly include those which have been removed from their naturally occurring environments, which environments can include arthropods, insects or whole live or dead infected mammals. Isolated Anaplasmataceae bacterial cells include thus; that, are contained within mammalian tissue that has been removed from a Anaplasmataceae bacteria-infected mammal. Isolated Anaplasmataceae bacterial cells also include those that are completely or partially separated from mammalian cells of a Anaplasmataceae bacteria-infected mammal, such as from lysing the host cells. Isolated Anaplasmataceae bacterial cells also include those that are contained within host cells as described herein, or separated partially or completely therefrom. Isolated Anaplasmataceae bacterial cells also include those that are substantially free of other microorganisms, e.g., in a culture.

"Isolated" as used in "isolated Anaplasmataceae bacterial immunogens" refers to bacterial immunogens that have been completely or partially separated from their respective source Anaplasmataceae bacteria. Compositions of isolated Anaplasmataceae bacterial immunogens can include some whole intact Anaplasmataceae bacteria, portions or components of Anaplasmataceae bacteria, whole intact host cell, and/or portions or components of host cells. Isolated Anaplasmataceae bacterial immunogens also include compositions that are enriched with respect to one or more Anaplasmataceae bacterial biomolecules.

"Anaplasmataceae bacterial immunogens" as used herein includes whole Anaplasmataceae bacteria that are inactivated or modified live bacteria. Anaplasmataceae bacterial immunogen as used herein can also include proteins (lipoproteins, membranous proteins, cytosolic proteins), immunogenic fragments of such proteins, nucleic acids, lipids, saccharides, lipopolysaccharides or other biological molecules derived from the Anaplasmataceae bacteria. Anaplasmataceae bacterial immunogen can be whole Anaplasmataceae bacterial cells or parts thereof that are present in host cells, wherein both the bacterial and host cells are killed or inactivated. Anaplasmataceae bacterial immunogen can also be whole Anaplasmataceae bacterial cells or parts thereof that are present in host cells, wherein the bacterial or host cells are not killed or inactivated.

The skilled artisan is generally familiar with the techniques by which bacterial or host cells can be killed or inactivated. Such techniques include, physical, chemical and biological means. Non-limiting examples of inactivation techniques include sonication, freeze-thaw techniques, pressure, treatment with heat, chemicals or enzymes. Non-limiting examples of chemical inactivation agents include treatment with binary ethyleneamine (BEA) and formalin (formaldehyde solution).

As stated above, the material cultured according to the present invention can be used to make antigen for vaccines. As used herein, the term "vaccine(s)" means and refers to a product, the administration of which is intended to elicit an immune response that can prevent and/or lessen the severity of one or more infectious diseases. A vaccine contains an antigen (or, "active agent," "immunogen," "therapeutic agent," or "immunogenic composition") that may be material cultured according to the present invention including a host cell infected with Anaplasmataceae bacteria, whole intact Anaplasmataceae bacteria, or bacterial fractions or parts or biomolecules of a Anaplasmataceae bacteria that act to stimulate the immune system in an animal. An antigen may be a live attenuated or killed preparation of Anaplasmataceae bacteria-infected host cells, live attenuated or killed Anaplasmataceae bacteria, living irradiated cells, crude fractions or purified Anaplasmataceae bacterial immunogens. Hence, a vaccine can comprise enriched, isolated or purified antigen. The vaccines can be made from inactivated or killed cultures of Anaplasmataceae infected host cells, or inactivated or killed Anaplasmataceae bacteria.

A vaccine may also comprise a combination of antigens from more than one Anaplasmataceae bacterial species or from other pathogens (e.g. viral, bacterial parasitical or fungal) as described further below.

Vaccines made from material cultured according to the present invention comprise a therapeutically effective amount of the antigen. In the context of this disclosure, a "therapeutically effective amount" refers to an amount of an antigen or vaccine that would induce an immune response in a mammal receiving the antigen or vaccine which is adequate to prevent or ameliorate signs or symptoms of disease, including adverse health effects or complications thereof, caused by infection with a pathogenic Anaplasmataceae bacterium. Humoral immunity or cell-mediated immunity or both humoral and cell-mediated immunity may be induced. The immunogenic response of an animal to a vaccine may be evaluated, e.g., indirectly through measurement of antibody titers, via microscopic analysis, or directly through monitoring signs and symptoms after challenge with wild type strain. The protective immunity conferred by a vaccine may be evaluated by measuring, e.g., reduction in clinical signs such as mortality, morbidity, body temperature and overall physical condition and overall health and performance of the subject. The amount of a vaccine that is therapeutically effective may vary depending on the particular virus used, or the condition of the subject, and may be determined by one skilled in the art.

The material cultured according to the present invention can also be used to make immunogenic compositions that stimulate an immune response in a subject mammal to which the compositions are administered. Such compositions can be used to identify antigens that can serve as the basis of a vaccine. Thus, for example, immunogenic compositions comprising material cultured according to, the present invention can be administered to a subject mammal. Thereafter, the antibody titer of the subject mammal can be monitored and candidate Anaplasmataceae bacterial antigens can be selected for use or further study in vaccines. Immunoactive compositions of the present invention include compositions that stimulate a humoral immune response and/or a cell-mediated immune response in the subject receiving a vaccine.

As used herein, an "immune response" refers to the subject mammal's active immunity response due to having received one or more vaccines based upon material cultured according to the methods described herein. The immune response can include the production of one or more antibody in response to the antigen or immunogen present in the vaccine. "Immune response" in a subject refers to the development of a humoral immune response, a cellular immune response, or a humoral and a cellular immune response to an antigen. Immune responses may be determined using standard immunoassays and neutralization assays, which are known in the art.

Vaccines made from material cultured according to the present invention can be used to prevent infection within a subject mammal, protect a subject mammal, or treat a subject mammal.

"Preventing infection" and like terms means to prevent or inhibit the replication of the bacteria which cause the identified disease, to inhibit transmission of the bacteria or virus, or to prevent the bacteria from establishing itself in its host animal, or to alleviate the symptoms of the disease caused by infection. The treatment is considered therapeutic if there is a reduction in bacterial load.

"Protection", "Protecting", and the like, as used herein with respect to a bacteria, means that the vaccine prevents or reduces the symptoms of the disease caused by the organism from which the antigen(s) used in the vaccine is derived. The terms "protection" and "protecting" and the like, also mean that the vaccine may be used to "treat" the disease or one of more symptoms of the disease that already exists in a subject.

"Treating" refers to reversing, alleviating, inhibiting the progress of, or preventing a disorder, condition or disease to which such term applies, or to preventing one or more symptoms of such disorder, condition or disease. Treating also refers to accelerating the recovery from an infection by one or more Anaplasmataceae organisms. "Treatment" refers to the act of "treating".

Hence, vaccines made from material cultured according to the present invention can be used to prevent Anaplasmataceae bacterial infection in a subject mammal, protect a subject mammal against Anaplasmataceae bacteria, and treat a subject mammal for Anaplasmataceae bacterial infection. Such prevention, protection or treatment can include (without limitation) reducing or eliminating the risk of infection by the pathogenic Anaplasmataceae organism, ameliorating or alleviating the symptoms of an infection by such Anaplasmataceae organism, reduction in Anaplasmataceae bacterial load, decreasing incidence or duration of Anaplasmataceae infections, reducing acute phase serum protein levels of Anaplasmataceae bacteria, reduced rectal temperatures, and/or increase in food uptake and/or growth, for example.

"Pharmaceutically acceptable" as used herein refers to substances (e.g., adjuvants, immunostimulants, carriers, diluents, emulsifying or stabilizing agents), which are within the scope of sound medical judgment, suitable for use in contact with the tissues of subjects without undue toxicity, irritation, allergic response, and the Like, commensurate with a reasonable benefit-to-risk ratio, and effective for their intended use. Pharmaceutically acceptable substances do not interfere with the effectiveness of the therapeutic agent and are not toxic to the subject to whom it is administered.

"Subject" or "subject mammal" refers to any animal having an immune system, which includes mammals such as humans, cats, cattle, horses, swine, and dogs.

Material cultured according to the present invention can also be used in diagnostic applications to diagnose the presence of diseases or illnesses caused by Anaplasmataceae bacteria. Non-limiting examples of such diagnostic applications include use of bacterial fractions, proteins or other biomolecules in antibody binding assays. The bacterial fractions, proteins or other biomolecules may also be used to generate polyclonal or monoclonal antibodies for such assays.

Host Cell Growth

Host cells for culturing bacterial organisms according to the present invention are first prepared prior to infecting with the desired bacterial organism. A sample of an isolated feline embryonic cell line is seeded into media for either suspended or adherent growth. As used herein, adherent growth conditions wherein a layer of cells coats surfaces contained within the vesicle in which the cells are cultured. The surfaces can include the interior surface of the vesicle itself, or surfaces of glass or polymeric beads contained within the vesicle to increase surface area. Microcarriers can also be used to increase surface area and host cell growth. In contrast to adherent growth, it may be possible to grow the host cells in suspension, in which the host cells need not bind to surfaces within the culturing vesicle.

The skilled artisan is generally familiar with the varieties of culturing media that may be used to grow up the host cells. The host cell growth media may be derived from animals. Alternatively, the host cell growth media may be vegetable or yeast based, and may be animal protein-free. The growth media may be derived from soy bean extracts or from other protein-rich plants or protein-rich plant food products including, for example, legumes. Non-limiting example of specific media useful for growing host cells include Eagle's Minimal Essential Media (MEM), Glasgow-Minimal Essential Media, RPMI1640, OptiMEM, AIM V.

The growth media can contain or be supplemented with fetal bovine serum (FBS), tryptose solution, lacto-albumin hydrosolate solution, L-glutamine, sodium bicarbonate; lactalbumin hydrolysate, Polymyxin B, sodium pyruvate, glucose, magnesium sulfate.

Fresh growth media can be refed or replenished to the host cells prior to or after infection or exposure of the host cells to the Anaplasmataceae bacteria.

Cells can be grown at 36-38° C. for 2-9 days at 5% $CO_2$.

Infecting the Host Cells

The host cells may be exposed to or infected with bacterial organisms of the Anaplasmataceae family by bringing the host cells into contact with other eukaryotic cells known to be infected with the bacterial organisms. The skilled artisan is familiar with determining whether such other eukaryotic cells from a mammal, for example, are infected with such bacterial organisms. The infected mammalian cells may be derived from any tissue, including the spleen, liver, pancreas, lungs, heart or other muscle tissue, brain, gall bladder, blood, kidneys, lymph nodes or stomach. The infected mammalian cells may be prepared from a tissue extract via blender homogenization in an appropriate isotonic solution. The homogenate can then be used to innoculate (i.e., infect) a culture of host cells, applied as a layer over the host cells or simply brought into contact with them.

Alternatively, the host cells may be exposed to or infected with isolated bacterial organisms of the Anaplasmataceae family. The skilled artisan is familiar with techniques of isolating such bacterial organisms, or can obtain stocks of isolated bacterial organisms from a biological depository.

The growth medium used to prepare host cells prior to contact with Anaplasmataceae bacteria may be the same as the medium used to propagate the host cells after such contact. The Anaplasmataceae bacteria-exposed (or infected) host cells may be cultured for up to 95 days, up to 35 days, or for about 5 to 10 days, to achieve a titer of $\geq 1\times10^4$ $TCID_{50}$ (Tissue Culture Infectious Dose), and then the culture may be harvested and processed.

Harvesting

The Anaplasmataceae bacterial infected host cells may be harvested by collecting the tissue cell culture fluids and/or cells. The host cells may be harvested from the media (and the culture vesicles) with the Anaplasmataceae bacterial cells contained with the walls of the host cells. Alternatively, during harvesting the concentration of the Anaplasmataceae bacteria may be enriched by techniques that improve the liberation of the infective bacterial cells from the growth substrate, e.g. sonication, freeze thawing, heating or chemical or selective enzymatic lysis of the eukaryotic host cells. An enriched harvest of Anaplasmataceae bacteria can include material that is free of host cells or host cell material. Alternatively, an enriched harvest of Anaplasmataceae bacteria can include material that contains host cells or host cell material.

Inactivating

The skilled artisan is generally familiar with the techniques by which bacterial or host cells can be killed or inactivated. Such techniques include, physical, chemical and biological means. Non-limiting examples of inactivation techniques include sonication, freeze-thaw techniques, pressure, treatment with heat, chemicals or enzymes. Non-limiting examples of chemical inactivation agents include treatment with binary ethyleneimine (BEI), formalin (formaldehyde solution), beta-propiolactone, merthiolate, gluteraldehyde, sodium dodecyl sulfate, or the like, or a mixture thereof. The host cells can also be inactivated by heat or psoralen in the presence of ultraviolet light. These chemical inactivation agents or physical inactivation means can also be used to inactivate the Anaplasmataceae bacterial cells after their having been extracted or separated from the host cells.

Formulating

The inactivated, infected host cells or enriched Anaplasmataceae bacterial cells can serve as the antigen and may be formulated as a liquid suspension or may be lyophilized for its use in the preparation of a vaccine against diseases caused by Anaplasmataceae organisms. Material cultured according to the present invention can be formulated with any pharmaceutically acceptable adjuvants, immunostimulants, carriers, diluents, emulsifying or stabilizing agents, non-limiting examples of which are discussed below. The skilled artisan, however, would recognize that other adjuvants, immunostimulants, carriers, diluents, emulsifying agents or stabilizing agents may be used in formulating vaccines based upon material cultured according to the present invention.

Adjuvants & Immunostimulants

An adjuvant in general is a substance that boosts the immune response of the target in a non-specific manner. Many different adjuvants are known in the art. Non-limiting examples of adjuvants that may be used in the formulation of a vaccine made with material cultured according to the present invention include aluminum salts (e.g., alum, aluminum hydroxide, aluminum phosphate, aluminum oxide), cholesterol, monophosphoryl lipid A adjuvants, amphigen, tocophenols, monophosphenyl lipid A, muramyl dipeptide, oil emulsions, glucans, carbomers, block copolymers, Avridine lipid-amine adjuvant, heat-labile enterotoxin from *E. coli* (recombinant or otherwise), cholera toxin, or muramyl dipeptide, Freund's Complete and-Incomplete adjuvant, vitamin E, non-ionic block polymers and polyamines such as dextransulphate, carbopol, pyran, saponins and saponin derivatives, block co-polymers, and adjuvants such as those identified in U.S. Pat. Nos. 4,578,269, 4,744,983, 5,254,339, which are all herein fully incorporated by reference. Non-limiting examples of peptides that can serve as adjuvants include muramyldipeptides, dimethylglycine, or tuftsin. Non-limiting examples of oils that can serve as adjuvants include mineral oil, vegetable oils or emulsions thereof.

Vaccines made from material cultured according to the present invention may be formulated as an oil-in water emulsions or as a water-in-oil emulsions. Non-limiting examples of oil-in-water emulsions include paraffin oil-in-water emulsions, or emulsions made from one or more of squalene, block copolymers of ethylene oxide and propylene oxide, polysorbate surfactants, and/or threonyl analogs of muramyl dipeptide.

Oils used as adjuvants may be metabolizable by the subject receiving the vaccine such as vegetable or animal oils. Such oils typically consist largely of mixtures of triacylglycerols, also known as triglycerides or neutral fats. These nonpolar, water insoluble substances are fatty acid triesters of glycerol. Triacylglycerols differ according to the identity and placement of their three fatty acid residues.

Adjuvants can also be non-metabolizable consisting of components that cannot be metabolized by the body of the animal subject to which the emulsion is administered. Non-metabolizable oils suitable for use in the emulsions of the present invention include alkanes, alkenes, alkynes, and their corresponding acids and alcohols, the ethers and esters thereof, and mixtures thereof. The individual compounds of the oil may be light hydrocarbon compounds, e.g., compounds having 6 to 30 carbon atoms. The oil may be synthetically prepared or purified from petroleum products. Non-limiting examples of non-metabolizable oils for use in the preparation of vaccines based upon material cultured according to the present invention include mineral oil, paraffin oil, and cycloparaffins, for example. The term "mineral oil" refers to a non-metabolizable adjuvant oil that is a mixture of liquid hydrocarbons obtained from petrolatum via a distillation technique. The term is synonymous with "liquefied paraffin", "liquid petrolatum" and "white mineral oil." The term is also intended to include "light mineral oil," i.e., oil which is similarly obtained by distillation of petrolatum, but which has a slightly lower specific gravity than white mineral oil.

Other compounds capable of enhancing a humoral immunity response that may be used in the formulation of vaccines based upon material cultured according to the present invention include, without limitation, ethylene maleic anhydrate (EMA) copolymer, latex emulsions of a copolymer of styrene with a mixture of acrylic acid and methacrylic acid.

In addition to the adjuvant, a vaccine based upon material cultured according to the present invention can include immunomodulatory agents such as, e.g., interleukins, interferons, or other cytokines (e.g., Th1-related cytokines, such as interleukin-12 (IL-12), interleukin-18 (IL-18), or gamma interferon).

The amount of adjuvant or immunostimulant added in a vaccine formulation based upon material cultured according to the present invention depends on the nature of the adjuvant or immunostimulant itself. The skilled artisan is capable of selecting an amount that is sufficient to enhance an immune response to the Anaplasmataceae bacterial immunizing agent.

Carriers

Pharmaceutically acceptable carriers suitable for use in vaccine formulated based upon material cultured according to the present invention may be any conventional liquid carrier suitable for veterinary pharmaceutical compositions, including balanced salt solutions such as are suitable for use in tissue culture media. Pharmaceutically acceptable carriers are understood to be compounds that do not adversely effect the health of the animal to be vaccinated, at least not to the extent that the adverse effect is worse than the effects seen when the animal is not vaccinated. Suitable carriers also include sterile water, saline, aqueous buffers such as PBS, solvents, diluents, isotonic agents, buffering agents, dextrose, ethanol, mannitol, sorbitol, lactose and glycerol, and the like.

Vehicle

Vaccines formulated from material cultured according to the present invention can also comprise a vehicle. A vehicle is a compound to which the host cells, Anaplasmataceae bacterial cells, or proteins, protein fragments, nucleic acids or parts thereof, adhere, without being covalently bound to it. Non-limiting examples of such vehicles include bio-microcapsules, micro-alginates, liposomes and macrosols. Some materials that serve as adjuvants can also serve as vehicles such as aluminum-hydroxide, aluminum phosphate, aluminum sulphate or aluminum oxide, silica, kaolin, and bentonite, all known in the art.

Stabilizers

Often, a vaccine is mixed with stabilizers, e.g. to protect degradation-prone components from being degraded, to enhance the shelf-life of the vaccine, or to improve freeze-drying efficiency. Non-limiting examples of stabilizers that may be added to vaccine formulations based upon material cultured according to the present invention include SPGA (Bovarnik et al., 1950, J. Bacteriology, vol. 59, p. 509), skimmed milk, gelatins, bovine serum albumin, carbohydrates (e.g. sorbitol, mannitol, trehalose, starch, sucrose, dextran or glucose), proteins (e.g., albumin, casein or degradation products thereof), non-animal origin stabilizers, and buffers (e.g. alkali metal phosphates). In lyophilized vaccine compositions, one or more stabilizers can be added.

Multivalent Vaccines

The immunogen harvested from the material cultured according to the present invention may be formulated in a vaccine comprising one or more additional immunogens. The additional immunoactive component(s) may be whole parasite, bacteria or virus (inactivated or modified live), or a fractionated portion or extract thereof (e.g., proteins, lipids, lipopolysacharide, carbohydrate or nucleic acid).

Where the immunogen harvested from the material cultured according to the present invention is used in a canine vaccine, antigens for other canine pathogens may be added into the formulation. Non-limiting examples of other pathogens for which additional antigens may be added include *Bordetella bronchiseptica*, canine distemper virus (CDV), canine adenovirus types 1 and 2 (CAV-1, CAV-2), canine parainfluenza (CPI) virus, canine coronavirus (CCV), canine parvovirus (CPV), *Leptospira interrogans* serovar *canicola, Leptospira interrogans* serovar *icterohaemorrhagiae, Leptospira interrogans* serovar *bratislava, Leptospira interrogans* serovar *pomona; Leptospira kirschneri* serovar *grippotyphosa*, rabies virus, *Borrelia burgdorferi*, canine rotavirus (CRV), canine herpesvirus (CHV), and Minute Virus of Canines (MVC), *Babesia canis, Giardia* and *Leishmania.*

Alternatively, a vaccine based upon material cultured according to the present invention may be administered simultaneously or concomitantly with other live or inactivated vaccines.

Freeze-Drying/Reconstitution

For reasons of stability or economy, vaccines based upon material cultured according to the present invention may be freeze-dried. In general this will enable prolonged storage at temperatures above 0° C., e.g. at 4° C. Procedures for freeze-drying are known to persons skilled in the art; equipment for freeze-drying at different scales is available commercially. To reconstitute the freeze-dried vaccine, it may be suspended in a physiologically acceptable diluent. Such diluents may be as simple as sterile water, or a physiological salt solution or other carrier as discussed above.

Dosaging

Vaccines based upon material cultured according to the present invention may be formulated in a dosage unit form to facilitate administration and ensure uniformity of dosage. Herein, a dosage unit as it pertains to the vaccine composition refers to physically discrete units suitable as unitary dosages for animals, each unit containing a predetermined quantity of Anaplasmataceae bacterial immunogen calculated to produce the desired immunogenic effect in association with the required adjuvant system and carrier or vehicle.

The effective immunizing amount of Anaplasmataceae bacterial immunogen can vary depending upon the chosen strain or strains and may be any amount sufficient to evoke a protective immune response. For example, amounts wherein the dosage unit comprises at least about $1\times10^4$ $TCID_{50}$ inactivated Anaplasmataceae bacterin are suitable.

Administering

Administration of the vaccine to a subject results in stimulating an immune response in the subject mammal. The route of administration for vaccines based upon material cultured according to the present invention may be administered to the mammalian target according to methods known in the art. Such methods include, but are not limited to, intradermal, intramuscular, intraocular, intraperitoneal, intravenous, oral, oronasal, and subcutaneous, as well as inhalation, suppository, or transdermal. Routes of administration include intradermal, intramuscular, intraperitoneal, oronasal, and subcutaneous injection. The vaccine may be administered by any means that includes, but is not limited to, syringes, nebulizers, misters, needleless injection devices, or microprojectile bombardment gene guns (Biolistic bombardment).

Alternative routes of application that are feasible are by topical application as a drop, spray, gel or ointment to the mucosal epithelium of the eye, nose, mouth, anus, or vagina, or onto the epidermis of the outer skin at any part of the body; by spray as aerosol, or powder. Alternatively, application may be via the alimentary route, by combining with the food, feed or drinking water e.g. as a powder, a liquid, or tablet, or by administration directly into the mouth as a liquid, a gel, a tablet, or a capsule, or to the anus as a suppository. The preferred application route is by intramuscular or by subcutaneous injection.

The vaccine according to the invention may be in several forms, e.g.: a liquid, a gel, an ointment, a powder, a tablet, or a capsule, depending on the desired method of application to the target.

The scheme of the application of the vaccine according to the invention to the target mammalian may be in single or multiple doses, which may be given at the same time or sequentially, in a manner compatible with the dosage and formulation, and in such an amount as will be immunologically effective.

Challenge Model

In order to effectively study and evaluate the pathogenic mechanisms of the Anaplasmataceae bacteria and the defense mechanisms of the host mammals and thereby to advance the vaccine art and improve vaccine products, an effective challenge model should be employed.

A challenge model for canine ehrlichiosis, for example, may be based upon the percentage of test animals to demonstrate persistent and severe clinical symptoms that are commonly associated with canine ehrlichiosis, such as fever, thrombocytopenia, mucopurulent ocular discharge, dehydration, or the like. Alternatively, the challenge model described by published U.S. Application No. 2006/0188524 (which is herein wholly incorporated by reference) may be employed. This *E. canis* challenge may be obtained in a test animal by administering to said test animal a challenge stock of peripheral blood mononuclear cells (PBMC) containing a virulent culture of live *E. canis* bacteria. The virulent *E. canis* culture is prepared by repeatedly passaging the *E. canis* microorganism such as *E. canis* Ebony, *E. canis* Broadfoot or the like, in a host; separating the PBMC from the host blood sample; and mixing the separated PBMC with 20% fetal bovine serum and 10% dimethyl sulfoxide.

A method for the induction of clinical canine ehrlichiosis in a test animal includes administering to said animal an effective amount of an *E. canis* challenge stock, consisting essentially of a virulent *E. canis* microorganism in peripheral blood mononuclear cells. Viable cultures of each of *E. canis* Broadfoot (sometimes referred to as *E. canis* BF, or Broadfoot), and *E. canis* Ebony (sometimes referred to as Ebony) have been deposited (Feb. 11, 2004) with the ATCC, 10801 University Boulevard, Manassas, Va. 20110-2209 U.S.A., and have been respectively given the ATCC accession numbers PTA-5811 for the Broadfoot strain, and PTA-5812 for the Ebony strain.

Several other cellular diagnostic methods exist to determine the presence of infection. For example, the presence of infection may be determined by direct immunofluorescence. Other methods to detect infection include staining, e.g., Giemsa, Wright/Giemsa. Acridine Orange can also be utilized to stain the organisms.

Unless defined otherwise, all technical and scientific terms used herein have the same meaning as commonly understood by one of ordinary skill in the art to which this invention belongs. All publications mentioned herein are hereby wholly incorporated by reference.

For a more clear understanding of the invention, the following examples are set forth below. These examples are merely illustrative and are not understood to limit the scope or underlying principles of the invention in any way. Indeed, various modifications of the invention, in addition to those shown and described herein, will become apparent to those skilled in the art from the examples set forth hereinbelow and the foregoing description. Such modifications are also intended to fall within the scope of the appended claims.

EXAMPLES

Example 1

Growth of *E. canis* on FEF Cells in the Presence of DH82 Cells 1.1 Propagation of Uninfected DH82 Cells One frozen vial of uninfected DH82 cells (American Type Culture Collection (ATCC) accession no. CRL-10389, P.O. Box 1549, Manassas, Va. 20108) was thawed, clarified, and used to inoculate a 75-$cm^2$ cell culture flask containing DH82 Growth Medium, and incubated at 37° C. with 5% $CO_2$. DH82 Growth Medium consists of Dulbecco's MEM base supplemented with 10% fetal bovine serum (FBS) and 1% HEPES. Upon formation of a monolayer, the cells were scraped into the growth medium, harvested, and centrifuged at 1,500 rpm for 10 min. The cell pellet was resuspended in 5 ml of fresh DH82 Growth Medium and split at a ratio ranging from 1:3 to 1:5.

1.2 Infection of Uninfected DH82 Cells with *E. canis*-Infected DH82 Cells

One frozen vial of *E. canis*-infected DH82 cells (ATCC accession no. CRL-10390) was thawed, clarified, and used to inoculate a 175-$cm^2$ cell culture flask containing a monolayer (80-90% confluent) with approximately $10^7$ uninfected DH82 cells in DH82 Growth Medium. *E. canis*-infected DH82 cultures were maintained by refeeding, i.e., replacing 50% of the spent culture medium with fresh DH82 Growth Medium as described above. *E. canis*-infected cultures were monitored by using either the Diff-Quik staining method on slides containing acetone-fixed cells according to the manufacturer's directions (VWR, West Chester, Pa. #47733-150) or a standard immunofluorescent antibody (IFA) technique. Briefly, plates containing acetone-fixed cells from *E. canis*-infected and uninfected DH82 cultures were incubated with a polyclonal *E. canis* dog serum, washed with PBS, incubated with fluorescein-labeled goat anti-dog IgG gamma (Kirkegaard and Perry #02-19-02), washed with PBS, and examined with a fluorescence microscope.

1.3 Propagation of Uninfected FEF Cells

One vial of frozen feline embryonic fibroblast (FEF) cells was thawed, clarified, and used to inoculate a 175-$cm^2$ cell culture flask containing FEF Growth Medium, and incubated at 37° C. with 5% $CO_2$. FEF Growth Medium consists of M6B8 medium (MEM base, Glasgow-MEM base, tryptose phosphate, tryptose, lacto-albumin hydrosolate, L-glutamine, and sodium bicarbonate) and 5% FBS. After incubation for 4-5 days, the cultures were ready for passage when the monolayer was 90-95% confluent. After treatment with 0.25% trypsin, the cells were split at a ratio of 1:5 to 1:10.

1.4 Infection of Uninfected FEF Cells with *E. canis*-infected DH82 Cells

*E. canis*-infected DH82 cells were harvested by scraping into the culture medium, centrifuged at 1,500 rpm for 10 min, and resuspended at $1\times10^6$ cells/ml in fresh DH82 Growth Medium. Uninfected FEF cultures that were seeded at $6\times10^6$ cells per 175-$cm^2$ cell culture flask in FEF Growth Medium and incubated for 18-24 hrs at 37° C. with 5% $CO_2$ were suspended in culture medium and placed in 75-$cm^2$ cell culture flasks at a split ratio of 1:3. Six ml of resuspended *E. canis*-infected DH82 cells were then used to infect each 75-$cm^2$ cell culture flask containing uninfected FEF cells in suspension, and incubated at 37° C. with 5%. $CO_2$. The *E. canis*-infected DH82/FEF mixed cultures were fed every three days by replacing spent culture medium with fresh FEF Growth Medium. At 14 days post-infection, the mix cultures were split 1:2 and cell suspensions were transferred into the wells of 24-well cell culture plates at 1 ml per well. Following incubation for 16 hrs at 37° C. with 5% $CO_2$, culture supernatant from the wells were transferred onto slides, fixed with acetone, and evaluated for presence of *E. canis* infection using IFA as described above.

Example 2

Growth of *E. canis* on a Homogenous Population of FEF Cells

Dogs were infected intravenously with 0.5-2 mL of *E. canis*-infected DH82 cells expanded from cells obtained from the ATCC as described above. Such *E. canis*-infected DH82 cells are described in U.S. Pat. No. 5,192,679, which is fully incorporated by reference herein. Dogs were positively identified as being infected with *E. canis* via PCR of spleen and blood DNA. DNA was purified from blood and tissue samples using a QIAamp DNA Mini Kit (Qiagen, Valencia, Calif.) according to the manufacturer's instructions. PCR was performed on a RoboCycle® robotic thermocycler (Stratagene, Cedar Creek, Tex.) using 25 μl reactions consisting of 2.5 μl of 10× reaction buffer (Genscript Corporation, Piscataway, N.J.), 0.2 μl of 100 mM dNTPs (Invitrogen Corp., Carlsbad, Calif.), 1 μl of 10 μM oligonucleotide primer 1 (5'-AGA ACG AAC GCT GGC GGC AAG C-3") and oligonucleotide primer 2 (5'-CGT ATT ACC GCG GCT GCT GGC A-3'), and 0.2 μl of 5 U/μl Taq polymerase (Genscript Corp.) in a thermocycling protocol consisting of a preliminary denaturation step of 94° C. for 5 min, followed by 35 cycles of 94° C. for 1 min, 60° C. for 1 min, and 72° C. for 1 min, followed by a final elongation step of 72° C. for 10 minutes. Homogenates in fresh growth medium were prepared from samples of spleens, lymph nodes, or peripheral blood mononuclear cells (PBMCs) obtained from *E. canis*-infected dogs and used as an overlay to infect FEF cells.

*E. canis*-infected spleen homogenate was inoculated into uninfected FEF cells in two separate 75-$cm^2$ cell culture flasks containing 30 ml of FEF cell suspension seeded at $2\times10^5$ cells/ml per flask bringing the homogenate to a final dilution of 1:10 to 1:100. Following 18-24 hours incubation at 37° C. with 5% $CO_2$, the culture medium was replaced with 30 mL of fresh FEF Growth Medium. After 5-7 days of incubation, the cell monolayer was trypsinized and resuspended in 5-10 nil of fresh FEF Growth Medium. Five mL of this suspension was then inoculated into each of two 175-$cm^2$ cell culture flasks containing 50 mL of FEF Growth Medium. Cells were then incubated for 7-10 days at 37° C. with 5% $CO_2$. To maintain viability, the cultures required "feeding", which was accomplished by replacing 50% of spent culture medium with fresh FEF Culture Medium. After 10-14 more days of incubation at 37° C. with 5% $CO_2$, the cells were trypsinized and resuspended as described above. To maintain continuous propagation, 1 to 2 mL of infected FEF cell suspension was passed onto uninfected FEF cells and incubated at 37° C. with 5% $CO_2$. Infected cultures were passed 7 to 13 times using incubation times ranging from 4 to 14 days. The presence of *E. canis* in the cultured FEF cells was confirmed by the use of IFA and PCR as described above.

Example 3

Growth of *E. canis* on a Homogenous Population of FCWF-4 Cells 3.1 Propagation of Uninfected FCWF-4 Cells (ATCC #CRL-2787)

One frozen vial of uninfected *felis catus* whoe fetus-4 (FCWF-4) cells (ATCC accession no. CRL-2787) was thawed, clarified, and used to inoculate a 75-$cm^2$ cell culture flask containing FCWF Growth Medium, and incubated at 37° C. with 5% $CO_2$. FCWF Growth Medium consists of E-MEM (Eagle's Minimal Essential medium with Earle's balanced salt solution and 2 mM L-glutamine), 1.0 mM sodium pyruvate, 0.1 mM nonessential amino acids, 1.5 g/liter sodium bicarbonate, and 10% FBS. After 4-5 days of incubation, the 90-95% confluent monolayer was treated with 0.25% trypsin and split at a ratio of 1:4 to 1:6.

3.2 Preparation of Homogenous Population of *E. canis*-infected FCWF-4 Cells

Prior to infection with *E. canis*, uninfected FCWF-4 cells were seeded into a 175-$cm^2$ flask at $6\times10^6$ cells per flask and incubated for 18-24 hrs. *E. canis*-infected spleen homogenate was used to infect FCWF-4 cells as described for FEF cells except the FCWF Growth Medium was used in place for the FEF Growth Medium. The presence of *E. canis* in the cultured FCWF-4 cells was confirmed by the use of IFA and PCR as described above Example 4

Growth of E. Marls on a Homogenous Population of FEA Cells 4.1 Propagation of Uninfected FEA Feline Embryonic Cells One vial of frozen uninfected FEA feline embryonic cells was thawed, clarified and used to inoculate a 75 $cm^2$ flask containing FEA Growth Medium, and incubated at 37° C. with 5% CO2. FEA Growth Medium consists of Dulbeccos MEM, 2 mM L-glutamine, 1.0 mM sodium pyruvate and 10% FBS. After 7 days of incubation, the confluent monolayer was treated with 0.25% trypsin and passed at a split ratio of 1:2.

4.2 Preparation of Homogenous Population of *E. Muris*-infected FEA Feline Embryonic Cells Uninfected DH82 cells were propagated as described above, and infected with *E. muris* using *E. muris*-infected DH82 cells (ATCC accession no. VR-1411—Asuke strain). The protocol for the preparation of materials and infection essentially followed the protocol as described above for *E. canis*-infected DH82 cells, except that *E. muris*-infected DH82 cells were substituted for *E. canis*-infected DH82 cells. Mice were infected intraperitoneally with 0.5 mL of *E. muris*-infected DH82 cells.

Mice were positively identified as being infected with *E. muris* via PCR of spleen and blood DNA. DNA was purified from blood and tissue samples using a Qiagen QIAamp DNA Mini Kit according to the manufacturer's instructions. PCR was performed on a RoboCycler® robotic thermocycler (Stratagene) using 25-μl reactions consisting of 2.5 μl of 10× reaction buffer (Genscript), 0.2 μl of 100 mM dNTPs (Invitrogen), 1 μl of 10 μM oligonucleotide primer 1 (5'-AGA ACG AAC GCT GGC GGC AAG C-3") and oligonucleotide primer 2 (5'-CGT ATT ACC GCG GCT GCT GGC A-3'), and 0.2 μl of 5 U/μl Taq polymerase (Genscript) in a thermocycling protocol consisting of a preliminary denaturation step of 94° C. for 5 min, followed by 35 cycles of 94° C. for 1 min, 60° C. for 1 min, and 72° C. for 1 min, followed by a final elongation step of 72° C. for 10 minutes.

Homogenates in fresh growth medium were prepared from spleen samples obtained from *E. muris*-infected mice and used in FEA feline embryonic cells. One ml of the *E. muris*-infected mouse spleen homogenate was inoculated into uninfected FEA feline embryonic cells in a 25 $cm^2$ cell culture flask containing a 24 hour FEA feline embryonic cell monolayer (at ~80% confluency) and 8 ml of FEA growth medium at a final homogenate dilution of 1:9. Following 5-24 hours incubation at 37° C. with 5% CO2, the culture medium was replaced with 8 ml of fresh FEA Growth Medium. After 5-7 days incubation, the cell monolayer was trypsinized and resuspended in 2 ml fresh FEA growth medium. One ml of this *E. muris*-infected cell suspension was inoculated into a 75 $cm^2$ cell culture flask containing a 24 hour FEA feline embryonic cell monolayer and 30 ml of FEA growth medium. Cells were incubated for 4-7 days at 37° C. with 5% $CO_2$. Infected cultures were passed 5 times using incubation times ranging from 4-9 days at 37° C. with 5% $CO_2$. For further passage, 1 to 2 ml of infected cells that were trypsinized and resuspended in 4 to 8 ml of growth medium was used to infect additional uninfected FEA feline embryonic cells. Infected cells were inoculated into flasks containing 24-hour-old FEA feline embryonic cell monolayer, incubated for 5-48 hrs at 37° C. with 5% $CO_2$, refed with fresh growth medium, and incubated further for 4-9 days at 37° C. with 5% $CO_2$. The presence of *E. muris* in the cultures of FEA feline embryonic cells was confirmed by the use of IFA and PCR, as described above.

Example 5

Growth of *E. muris* on a Homogenous Population of FEF Cells

Homogenates in growth medium were prepared from spleen samples obtained from *E. muris*-infected mice as described above and was used to infect FEF cells, cultured as described above. Each uninfected cell line was inoculated with 0.5 ml *E. muris*-infected spleen homogenate per 25 $cm^2$ cell culture flask which contained a 24 hour monolayer and 8 ml growth medium. This is a final homogenate dilution of 1:17. Following 24 hours incubation at 37° C. with 5% $CO_2$, the culture medium was replaced with 8 ml of appropriate fresh culture medium. After 7 days incubation, the cell monolayer was trypsinized and the entire infected cell contents of the 25 $cm^2$ flask was inoculated into a 75 $cm^2$ flask containing 30 ml fresh medium (this is a 1:3.75 split). Infected cultures were passed 2 times using incubation times ranging from 7-8 days at 37° C. with 5% $CO_2$. The presence of *E. muris* in the cultures of cells was confirmed by the use of IFA and PCR, as described above.

Example 6

Growth of *E. muris* on a Homogenous Population of FCWF-4 Cells

Homogenates in growth medium were prepared from spleen samples obtained from *E. muris*-infected mice as described above and was used to infect FCWF-4 cells, cultured as described above. Each uninfected cell line was inoculated with 0.5 ml *E. muris*-infected spleen homogenate per 25 $cm^2$ cell culture flask which contained a 24 hour monolayer and 8 ml growth medium. This is a final homogenate dilution of 1:17. Following 24 hours incubation at 37° C. with 5% $CO_2$, the culture medium was replaced with 8 ml of appropriate fresh culture medium. After 7 days incubation, the cell monolayer was trypsinized and the entire infected cell contents of the 25 $cm^2$ flask was inoculated into a 75 cm2 flask containing 30 ml fresh medium (this is a 1:3.75 split). Infected cultures were passed 2 times using incubation times ranging from 7-8 days at 37° C. with 5% $CO_2$. The presence of *E. muris* in the cultures of cells was confirmed by the use of IFA and PCR, as described above.

Example 7

Infection of FEF Cells with *N. risticii*-infected P388D1 Cells

Materials for infecting FEF cells with *N. risticii* from *N. risticii*-infected P388D1 cells can be prepared as described above, or as previously described in Vemulapalli, R. et al., J. Clin. Micro. 33(11): 2987-2993 (1995), or as previously described in U.S. Pat. No. 4,759,927, which is herein wholy incorporated by reference.

P388D1 cells (ATCC accession no. CC1-46) infected with the 90-12 strain of *N. risticii* were added at a multiplicity-of-infection (MOI) of 0.0006 to 0.0028 in 850-$cm^2$ roller bottles containing monolayers of 3-4-day-old FEF cells. Prior to infection, the spent culture medium in the roller bottles were replaced with 300 ml of the culture medium used for infection. After inoculation at the specified MOI, the roller bottles were incubated at 37° C. without $CO_2$. Culture medium tested included but not limited to D-MEM, MEM Earles, and M6B8; 0 to 5% FBS was used. The infected cultures were harvested when the cytopathic effect (CPE) reached 75% to 85%, which ranged from 8-16 days depending on the MOI used. CPE observed included swelling, rounding, and detachment of infected cells. The cultures were harvested by tapping the sides of roller bottles to dislodge the cells into the culture medium. The presence of infection was confirmed using a standard IFA protocol on cells that were fixed with 70% acetone and 30% methanol in 96-well plates with an *N. risticii* monoclonal antibody and fluorescein-labeled goat anti-mouse IgG (Bethyl Laboratories, Inc., Montgomery, Tex.).

Example 8

Infection of MA-104 Cells with *E. Muris*

8.1. Propagation of Uninfected MA-104 Cells

One vial of frozen MA-104 cells (monkey embryo kidney epithelial cells, ATCC accession no. CRL-2378.1) was thawed, clarified, and used to inoculate a 75-$cm^2$ cell culture flask containing MA-104 Growth Medium, and incubated at 37° C. with 5% $CO_2$. MA-104 Growth Medium consists of Eagles Minimal Essential medium with Earles BSS and 2 mM L-glutamine (EMEM) which is supplemented with 1.0 mM sodium pyruvate, 0.1 mM nonessential amino acids, 1.5 g/1 sodium bicarbonate, an additional 1% L-glutamine and 10% FBS. After incubation for 5-7 days, the cultures were ready for passage when the monolayer was 90-95% confluent. After treatment with 0.25% trypsin, the cells were passed at a split ratio of 1:5 to 1:10.

8.2. Preparation of Homogenous Population of *E. Muris*-Infected MA-104 Cells

Homogenates were prepared from spleen samples obtained from *E. muris*-infected mice and used to infect MA-104 cells. *E. muris*-infected mouse spleen homogenate was used to overlay MA-104 cells in 25-cm2 cell culture flasks. Twenty-four hour old MA-104 monolayers at ~85% confluency were inoculated with a 1:91 dilution of spleen homogenate (0.1 ml spleen homogenate into 9 ml existing 24 hour flask media).

MA-104 Growth Medium consists of Eagles Minimal Essential medium with Earles BSS and 2 mM L-glutamine (EMEM) which is supplemented with 1.0 mM sodium pyruvate, 0.1 mM nonessential amino acids, 1.5 g/1 sodium bicarbonate, an additional 1% L-glutamine and 10% FBS. After 5 days of incubation at 37° C. with 5% $CO_2$, the cells were treated with trypsin and all the cells were resuspended in 30 ml of fresh MA-104 Growth Medium; this 30 ml was then dispensed into a 75 $cm^2$ cell culture flask. After 8 days of incubation at 37° C. with 5% $CO_2$, these cells were treated with trypsin and all the cells were resuspended in 50 ml of fresh MA-104 Growth Medium; this 50 ml was then dispensed into a 175 $cm^2$ cell culture flask. For further passage, 3 mLs of infected cells that were trypsinized and resuspended in 9-10 ml of growth medium were inoculated into fresh 50 ml growth medium in 175 $cm^2$ cell culture flasks. Uninfected MA-104 cells were added during passaging when the cytopathic effect in the infected cells appeared advanced, the infected cells were sparse, or the infected cells appeared weak. The incubation range for the infected cells was 5-8 days at 37° C. with 5% $CO_2$. The presence of *E. muris* in the cultured MA-104 cells was confirmed by use of IFA.

* * *

All patents, published patent application and other publications are herein incorporated by reference in their entirety.

We claim:

1. A method for continuously culturing an *Ehrlichia* species comprising:

i) obtaining the *Ehrlichia* species;

ii) obtaining feline embryonic fibroblast cells;

iii) infecting the feline embryonic fibroblast cells with the *Ehrlichia* species; and iv) continuously culturing said feline embryonic fibroblast cells in feline embryonic cell growth medium under conditions conducive to propagating the feline embryonic fibroblast cells, thereby continuously culturing the *Ehrlichia* species.

2. A method for continuously culturing an *Ehrlicia* species comprising:

i) infecting a mammal with the *Ehrlicia* species;

ii) obtaining infected tissue from the infected mammal;

iii) contacting feline embryonic fibroblast cells with the infected tissue; and iv) continuously culturing said feline embryonic fibroblast cells in feline embryonic cell growth medium under conditions conducive to propagating the feline embryonic fibroblast cells, thereby continuously culturing the *Ehrlichia* species.

3. The method of claim 2, wherein the infected tissue from the infected mammal is a spleen homogenate.

4. A method for continuously culturing a *Neorickettsia ristícii* species comprising:

i) infecting a mammal with the *Neorickettsia risticii* species;

ii) obtaining infected tissue from the infected mammal;

iii) contacting feline embryonic fibroblast cells with the infected tissue; and iv) continuously culturing said feline embryonic fibroblast cells in feline embryonic cell growth medium under conditions conducive to propagating the feline embryonic fibroblast cells, thereby continuously culturing the *Neorickettsia risticii* species.

5. The method of claim 4, wherein the infected tissue from the infected mammal is a spleen homogenate.

6. A method for continuously culturing *Neorickettsia risticii* species comprising:

i) obtaining the *Neorickettsia risticii* species;

ii) obtaining feline embryonic fibroblast cells;

iii) infecting the feline embryonic fibroblast cells with the *Neorickettsia risticii* species; and iv) continuously culturing said feline embryonic fibroblast cells in feline embryonic cell growth medium under conditions conducive to propagating the feline embryonic fibroblast cells, thereby continuously culturing the *Neorickettsia risticii* species.

* * * * *

SEQUENCE LISTING

```
<160> NUMBER OF SEQ ID NOS: 2

<210> SEQ ID NO 1
<211> LENGTH: 22
<212> TYPE: DNA
<213> ORGANISM: unknown
<220> FEATURE:
<223> OTHER INFORMATION: Sequence used in Example 2

<400> SEQUENCE: 1

agaacgaacg ctggcggcaa gc                                              22


<210> SEQ ID NO 2
```

-continued

```
<211> LENGTH: 22
<212> TYPE: DNA
<213> ORGANISM: unknown
<220> FEATURE:
<223> OTHER INFORMATION: Sequence used in Example 2

<400> SEQUENCE: 2

cgtattaccg cggctgctgg ca                                             22
```